US005753435A

United States Patent [19]

Aharonowitz et al.

[11] Patent Number: 5,753,435
[45] Date of Patent: *May 19, 1998

[54] **OXIDO REDUCTASE ENZYME SYSTEM OBTAINABLE FROM *P. CHRYSOGENUM*, THE SET OF GENES ENCODING THE SAME AND THE USE OF OXIDO REDUCTASE ENZYME SYSTEMS OR GENES ENCODING THE SAME FOR INCREASING ANTIBIOTIC PRODUCTION**

[75] Inventors: Yair Aharonowitz, Hod-Hasheron, Israel; Lucia Helena Maria Van Der Voort, Rÿswÿk, Netherlands; Gerald Cohen, Hod-Hasharon, Israel; Reolof Ary Lans Bovenberg, Rotterdam, Netherlands; Rachel Schreiber, Herzelia, Israel; Anat Argaman, Rosh-Haain, Israel; Yossef Av-Gay, Yahud, Israel; Helena Maria Nan, Nootdorp; Alfred Kattevilder, Delft, both of Netherlands; Harriet Palissa, Berlin; Henk Van Liempt, Bonn, both of Germany

[73] Assignee: Gist-Brocades, Delft, Netherlands

[*] Notice: The term of this patent shall not extend beyond the expiration date of Pat. No. 5,652,132.

[21] Appl. No.: 386,729

[22] Filed: Feb. 10, 1995

Related U.S. Application Data

[60] Continuation-in-part of Ser. No. 274,043, Jul. 12, 1994, Pat. No. 5,652,132, which is a division of Ser. No. 820,688, Mar. 24, 1992, Pat. No. 5,328,839.

[30] Foreign Application Priority Data

Jun. 18, 1990 [EP] European Pat. Off. ............... 90201598

[51] Int. Cl.$^6$ .............. C12Q 1/68; C12N 9/06; C12N 15/53
[52] U.S. Cl. .............. 435/6; 435/191; 435/252.3; 435/252.33; 435/252.35; 435/254.11; 435/419; 435/325; 536/23.2
[58] Field of Search ................. 435/191, 252.3, 435/252.33, 252.35, 254.11, 240.1, 240.2, 240.4, 419, 6, 325; 536/23.2

[56] References Cited

U.S. PATENT DOCUMENTS 5,328,839  7/1994  Aharonowitz et al. ............ 435/191

FOREIGN PATENT DOCUMENTS

0354624AZ  2/1990  European Pat. Off. ........ C12N 15/00

OTHER PUBLICATIONS

Holmgren, A., *Ann. Rev. Biochem.* "Thioredoxin" (1985) 54:237–271.

Cohen et al., *J. Bacteriol.*, Feb. 1994, pp. 973–984.

Russell et al. *J. Biol. Chem.* 263(18): 9015–9019, Jun. 25, 1988.

*Primary Examiner*—Keith D. Hendricks
*Attorney, Agent, or Firm*—McDonnell Boehnen Hulbert & Berghoff

[57] ABSTRACT

A new oxido reductase enzyme activity obtainable from *P. chrysogenum*, involved in the production of β-lactams, the set of genes encoding said enzyme activity, and a method to enhance said production by using the above-mentioned oxido reductase system and other oxido reductase systems or genes encoding for the same are disclosed.

12 Claims, 7 Drawing Sheets

```
1                  10                  20                  30                  40                  50                  60
GCCTCGGTCTCTCCAAGTCATTCCGAGCGTCGGCGTCGGTCAATTCCAATACCGCCAGAAT
                                                            Me 70                  80                  90                 100                 110                 120
GGTGCACTCTAAAGTAGTCAgtaagtggttttcgaggagatcgatgatccggatcacc
tValHisSerLysValValI 130                 140                 150                 160                 170                 180
tagatttcttcgatcagagttctaaccgttttccccacagTTATTGGCTCCGGCCCT
                                        leIleGlySerGlyPro 190                 200                 210                 220                 230                 240
GGTGCCCACACTGGCTATCTATCTATCGGCGCAGAGCTCCAGCCAGTCCTTTACGAG
GlyAlaHisThrAlaAlaIleTyrLeuSerArgAlaGluLeuGlnProValLeuTyrGlu 250
GGCATGCTCG
GlyMetLeu
```

FIG. 2

```
                                        G GAT CCA TTG GGT TGA CTG   -100

CCA CTG CGG CCA CTA CCC TTC ACC AAC AAT CTC CTC CTT CGG             -58

CCT CGG TCT TCT CCA AGT CAT TTC CGA GCG TCG CGC GTC AAT             -16

TCC AAT ACC GCC AGA ATG GTG CAC TCT AAA GTA GTC Agt aag              27
                    M   V   H   S   K   V   V tgg ttt ttc gag gag atg gaa tga tcc gga tca cct aga ttt              69
                        intron I ctt cga tat cag agt tct aac cgt ttt ccc cca cag TT ATT              110
                                                   I   I GGC TCC GGC GCT GGT GCC CAC ACT GCC GCT ATC TAT CTA TCG             152
 G   S   G   P   G   A   H   T   A   A   I   Y   L   S CGC GCA GAG CTC CAG CCA GTC CTT TAC GAG GGC ATG CTC GCC             194
 R   A   E   L   Q   P   V   L   Y   E   G   M   L   A AAC GGT ACC GCC GCC GGT GGT CAG CTC ACG ACG ACC ACT GAC             236
 N   G   T   A   A   G   G   Q   L   T   T   T   T   D GTC GAG AAC TTC CCC GGA TTC CCC AGC GGC ATC GGC GGC GCC             278
 V   E   N   F   P   G   F   P   S   G   I   G   G   A GAG CTC ATG GAC AAC ATG CGC GCC CAA TCC GAG CGC TTC GGC             320
 E   L   M   D   N   M   R   A   Q   S   E   R   F   G ACC GAG ATC ATC ACA GAG ACC ATC TCC AAG CTT GAC CTC TCC             362
 T   E   I   I   T   E   T   I   S   K   L   D   L   S TCC CGG CCC TTC AAG ATG TGG ACC GAG TGG AAC GAT GAC GAA             404
 S   R   P   F   K   M   W   T   E   W   N   D   D   E GGC AGC GAG CCC GTC CGC ACC GCC GAC GCC GTC ATC ATT GCC             446
 G   S   E   P   V   R   T   A   D   A   V   I   I   A ACA GGC GCC AAC GCC CGC CGT CTG AAC CTG CCC GGC GAG GAG             488
 T   G   A   N   A   R   R   L   N   L   P   G   E   E
```

FIG. 3A

```
ACC TAC TGG CAG AAC GGA ATC AGC GCC TGT GCC GTC TGC GAC   530
 T   Y   W   Q   N   G   I   S   A   C   A   V   C   D

GGT GCC GTG CCC ATT TTC CGT AAC AAG CCC CTG TAC GTC ATT   572
 G   A   V   P   I   F   R   N   K   P   L   Y   V   I

GGC GGT GGT GAC TCC GCC GCC GAG GAG GCC ATG TTC CTG GCC   614
 G   G   G   D   S   A   A   E   E   A   M   F   L   A

AAG TAC GGC AGC AGC GTG ACT GTT CTC GTT CGC AAG GAC AAG   656
 K   Y   G   S   S   V   T   V   L   V   R   K   D   K

CTG CGT GCC TCT AAC ATC ATG GCT GAT CGT CTC CTT GCC CAC   698
 L   R   A   S   N   I   M   A   D   R   L   L   A   H

CCC AAG TGC AAG GTC CGC TTC AAC ACC GTC GCC ACC GAG GTT   740
 P   K   C   K   V   R   F   N   T   V   A   T   E   V

ATC GGC GAG AAC AAG CCT AAC GGC CTC ATG ACC CAC CTC CGT   782
 I   G   E   N   K   P   N   G   L   M   T   H   L   R

GTC AAG GAC GTT CTC TCT AAC GCG GAG GAG GTC GTT GAG GCT   824
 V   K   D   V   L   S   N   A   E   E   V   V   E   A

AAC GGT CTC TTC TAC GCT GTT GGT CAC GAC CCC GCC AGT GGT   866
 N   G   L   F   Y   A   V   G   H   D   P   A   S   G

CTC GTC AAG GGC CAG GTT GAG CTC GAC GAC GAG GGA TAC ATC   908
 L   V   K   G   Q   V   E   L   D   D   E   G   Y   I

ATC ACC AAG CCC GGT ACT AGC TTC ACT AAC GTC GAG GGT GTT   950
 I   T   K   P   G   T   S   F   T   N   V   E   G   V

TTC GCC TGC GGT GAT GTT CAG GAT AAG CGC TAC CGT CAG GCT   992
 F   A   C   G   D   V   Q   D   K   R   Y   R   Q   A

ATC ACC AGT GCC Ggt atg ttc ata ctt cag cat ctc att cat  1034
 I   T   S   A
```

FIG. 3B

```
agt aat tgc aat ttg gct aac tca ata ttc tac cag GA TCT  1075
                        intron II                 G  S GGC TGT GTC GCT GCT CTT GAG GCT GAG AAG TTC ATC GCC GAG  1117
 G   C   V   A   A   L   E   A   E   K   F   I   A   E ACC GAG ACT CAC CAG GAG GCA AAG CCT GTG CTC TAA ATA TAT  1159
 T   E   T   H   Q   E   A   K   P   V   L   Z

ATA CAC CCT TTC TCC TAC TGT TCT CTC CTA TTT CTC GTT GTC  1201

ATG ATG CAT GAA ACA TGA TGT TTG GCG CGT GTA TCG AGG ATT  1243

CTT CTT GCT TCT AGA CTT ATA TCT GTT TTA TGC GAT GAC TCT  1285

AGA GGA TCC CCG GGT ACC GA                                1305
```

FIG. 3C

OXIDO REDUCTASE ENZYME SYSTEM OBTAINABLE FROM P. CHRYSOGENUM, THE SET OF GENES ENCODING THE SAME AND THE USE OF OXIDO REDUCTASE ENZYME SYSTEMS OR GENES ENCODING THE SAME FOR INCREASING ANTIBIOTIC PRODUCTION

CROSS-REFERENCE TO RELATED APPLICATIONS

This application is a continuation-in-part application of U.S. application Ser. No. 08/274,043, filed Jul. 12, 1994, now U.S. Pat. No. 5,652,132, which is a divisional of U.S. application Ser. No. 07/820,688 filed on Mar. 24, 1992, now U.S. Pat. No. 5,328,839.

FIELD OF THE INVENTION

The present invention relates to an enzyme system involved in the production of β-lactam compounds and to the use of enzyme systems for increasing antibiotic production.

BACKGROUND

Penicillins and cephalosporins are the most widely used antibacterial agents. Penicillins and cephalosporins are secondary metabolites which are industrially produced by filamentous fungi like *Penicillium chrysogenum* and *Acremonium chrysogenum*, respectively, in several enzymatic steps (J. R. Miller and T. D. Ingolia, *Mol. Microbiol.* (1989) 3:689–695).

The main steps in the biosynthetic pathways leading to cephalosporins and penicillins have been elucidated in the past 30 years. The pathways share two enzymatic steps. In the first step a tripeptide is formed from α-aminoadipic acid, cysteine and valine. The enzyme which is responsible for this step is δ-(L-β-amino-adipyl)-L-cysteinyl-D-valine (ACV) synthetase. In the second step the ACV is cyclised by the action of isopenicillin N synthetase (hereinafter referred to as IPNS) or cyclase. The reaction product is isopenicillin N, a compound which contains the typical β-lactam ring structure and which possesses antibacterial activity. The biosynthesis of penicillin involves a unique third and last step in which the β-aminoadipic acid side-chain of isopenicillin N is exchanged for a hydrophobic sidechain. The hydrophobic side-chains commonly used in industrial production are phenylacetic acid (PAA) and phenoxyacetic acid (POA) yielding penicillin G and penicillin V, respectively. The side-chain exchange has been proposed to be a reaction catalyzed by a single enzyme referred to as acyltransferase (AT). Cephalosporins are formed from isopenicillin N in a number of steps including epimerization of isopenicillin N to penicillin N, ring expansion and hydroxylation.

The biosynthetic pathways to penicillins and cephalosporins have almost completely been elucidated and most of the enzymes involved in the biosynthesis towards penicillins and cephalosporins have been purified and characterized (Ingolia et al., *Med. Res. Rev.*, (1989) 9:245–256). The genes encoding these enzymes have been cloned and it is commonly accepted that the introduction of expression vectors containing DNA encoding these enzymes into production strains may improve the yield of α-lactam compounds. Recently, an example of the successful application of the expression of extra copies of genes has been described (Skatrud et al., *Biotechnology*, (1989) 7:477–485).

It has been recognized that maintaining reducing conditions is important for producing β-lactam compounds. For instance, under non-reducing conditions the tripeptide ACV dimerizes into ACV disulphide (bis-ACV) or possibly into mixed disulphides with other thiol-containing compounds. These disulphides are not used as substrates by IPNS. Furthermore, the enzyme IPNS active in non-reducing conditions (Perry et al., *Biochem. J.*, (1988) 255:345–351). Reducing compounds such as dithiothreitol (DTT) are used to maintain reducing conditions in vitro. In this way a process for producing cephalosporins from tripeptide precursors as well as unnatural penicillin and cephalosporin derivatives using isolated enzymes has been developed U.S. Pat. No. 4,510,246 and U.S. Pat. No. 4,536,476). Moreover, a process for producing tripeptides using the enzyme ACVS has been described in EP-A-280051. It is not known how enzymes and disulphide compounds, for instance ACV, involved in the production of β-lactam compounds are maintained in a reduced state in *P. chrysogenum* or other β-lactam producing microorganisms. Surprisingly an as yet unreported enzyme system with reducing properties which is able to reduce bis-ACV amongst other disulphide compounds, has been isolated. The enzyme system comprises two polypeptide components, a high and a low molecular weight polypeptide, and an electron carrier, such as nicotinamide adenine dinucleotide phosphate (NADPH), in its reduced form. The polypeptide components share similarity with thioredoxin reductase and thioredoxin, respectively. It has not previously been mentioned that the thioredoxin system might be involved in β-lactam production.

Therefore, the present invention provides an oxido reductase system, viz. a thioredoxin reductase system which is obtainable from *P. chrysogenum*, which is able to reduce ACV disulphide amongst other compounds is provided. This oxido reductase system consists of a high molecular weight (HMW) polypeptide with a molecular weight of about 36 kDa as determined by sodium dodecylsulphate polyacrylamide gel electrophoresis (SDS-PAGE), and a low molecular weight (LMW) polypeptide with a molecular weight of about 12 kDa as determined by SDS-PAGE, and a reduced electron carrier. The high and the low molecular weight polypeptides have been isolated by a combination of gel chromatography, ion-exchange chromatography and affinity chromatography. The HMW component is similar to the thioredoxin reductase obtained from *Escherichia coli*. The LMW component is similar to known thioredoxin, and possesses similar activities including protein disulphide exchange. Also provided for are the genes encoding the polypeptide compounds of the new oxido reductase system obtainable from *P. chrysogenum*.

Furthermore, the oxido reductase system of *P. chrysogenum* has been found to be involved in maintaining enzymes and disulphide compounds, for instance ACV, involved in β-lactam biosynthesis in a reduced state. Also other thioredoxin systems have been found to be applicable for this objective. In this way these systems are applicable in the in vitro production of agents, for instance in the production of β-lactam antibiotics. Also, genes encoding up to the entire sequence of both the polypeptide components of the new oxido reductase system obtainable from *P. chrysogenum* and those of the (other) thioredoxin systems can be used in a method to increase the production of metabolites, for instance β-lactam compounds, by growing a microorganism culture consisting of transformants of said microbial host comprising DNA sequences encoding first and second components or functional portions thereof of a thioredoxin system, each DNA sequence under the regulatory control of transcriptional and translational regulatory signals functional in said cells, whereby said components of said enzyme system are expressed and said β-lactam compound is produced; and isolating said β-lactam compound. The present invention further provides DNA constructs comprising at least one gene encoding up to the entire sequence of a polypeptide compound of the new oxido reductase system and a host comprising said construct. Finally, a method for reducing disulphide compounds and compounds involved in the production of β-lactam compounds in vitro has been provided for by contacting, in the presence of a reduced electron carrier, the compounds to be reduced with a composition comprising an oxido reductase system, consisting of a HMW polypeptide and a LMW polypeptide, and being capable of reducing disulphide compounds, or with a LMW polypeptide in the presence of a reducing agent as for instance DTT. Preferably, ACV is reduced in vitro in this way.

BRIEF DESCRIPTION OF THE FIGURES

FIG. 2 [SEQ ID NO:1] shows a partial nucleotide sequence of the P. chrysogenum HMW gene. The open reading frame encoding the N-terminal HMW amino acid sequence is indicated (underlined). The position of an intron is also indicated (undercast).

FIG. 3 [SEQ ID NO:6] shows the nucleotide sequence of the P. chrysogenum trxB (HMW) gene.

BRIEF DESCRIPTION OF THE SEQUENCE LISTINGS

Figure 1:
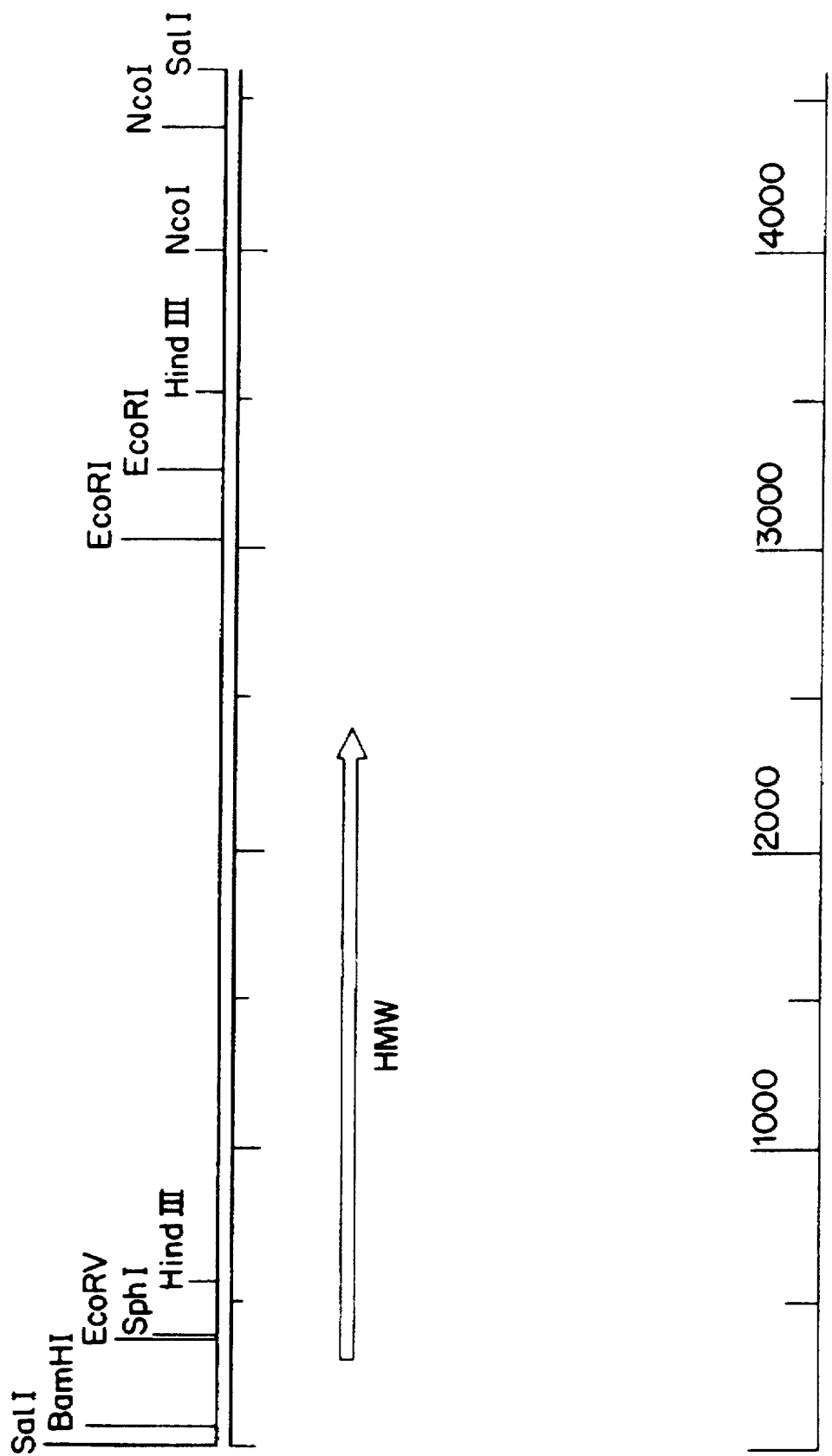
FIG. 1 shows a schematic representation of a partial restriction map of the P. chrysogenum derived DNA contained in pPCH-1. The position of the 5'-end of the gene and the direction of transcription of the HMW gene is indicated (arrow).

Sequence listing No. 1 shows part of the nucleotide sequence and deduced amino acid sequence of the P. chrysogenum HMW polypeptide.

Sequence listing No. 2 (FIG. 2) shows part of the amino acid sequence of the P. chrysogenum HMW polypeptide.

Sequence listing No. 3 shows part of the amino acid sequence of the P. chrysogenum LMW polypeptide.

Sequence listing No. 4 shows a 29-mer oligonucleotide probe, based upon the N-terminal amino acid sequence of the HMW polypeptide of P. chrysogenum.

Sequence listing No. 5 shows the redox sequence typical for thioredoxins.

Sequence listing No. 6 (FIG. 3) shows the entire nucleotide sequence and deduced amino acid sequence of the P. chrysogenum trxB (HMW) gene.

Sequence listing No. 7 shows the amino acid sequence of the P. chrysogenum HMW polypeptide.

Sequence listing No. 8 shows a 29-mer oligonucleotide probe, based upon the N-terminal amino acid sequence of the LMW polypeptide of P. chrysogenum.

Sequence listing No. 9 shows the entire nucleotide sequence and deduced amino acid sequence of the P. chrysogenum trxA (LMW) gene.

Sequence listing No. 10 shows the amino acid sequence of the P. chrysogenum LMW polypeptide.

Sequence listing No. 11 shows the amino acid sequence of the P. chrysogenum HMW polypeptide.

BRIEF DESCRIPTION OF THE SPECIFIC EMBODIMENTS

In accordance with the subject invention, an oxido reductase enzyme system is provided which can be used to obtain or to enhance β-lactam antibiotic production. The subject enzyme system is a naturally occurring enzyme system, which comprises two components, a high molecular weight polypeptide component and a low molecular weight polypeptide component, in isolated form and an electron carrier such as NADPH in a reduced state. As measured by SDS-PAGE, the high molecular weight (HMW) component of the oxido reductase system from P. chrysogenum has an apparent molecular weight of about 36 kDa, and the low molecular weight (LMW) component has an apparent molecular weight of about 12 kDa. The enzyme system is capable of forming free thiols in compounds containing disulphide bonds, in the presence of an electron donor such as NADPH.

The enzyme system will comprise two polypeptide components which, when combined in the presence of a suitable electron carrier in reduced form, are capable of maintaining enzymes and intermediates in a reduced state in vitro. Activity was demonstrated by the reduction of 5,5'-Dithiobis-(2-nitrobenzoic acid) (DTNB) by following the increase of absorbance at 412 nm at 25° C. Alternatively other substrates were used and the rate of reduction was measured by following the decrease of absorbance of NADPH at 340 nm. In this case activity is expressed as pmoles of NADPH/min/mg protein.

The subject enzyme system was obtained from P. chrysogenum, or from other yeasts, fungi or bacteria comprising the genes encoding the HMW or LMW component of P. chrysogenum after transfer and expression of the genes of the invention into a host microorganism.

The polypeptide components involved in reductase activity have been purified from cell-free extracts of P. chrysogenum. P. chrysogenum was grown on, for instance, a complex medium with for example starch as the carbon source, or on defined media. The optimum enzyme activity is dependent on the strain and the medium used, and the time of harvest of the mycelium, which can be determined empirically by one of skill in the art.

The polypeptide compounds of the subject enzyme system were isolated from cell-free extracts by combining a variety of techniques, including molecular sieving, ion exchange chromatography and affinity chromatography. The enzyme system was extracted from P. chrysogenum by an initial disruption of the cells, followed by homogenization in a low ionic strength (1 to 50 mM) buffer (for example a Tris buffer) at approximately pH 8.0. Lysis of cells can be performed in several ways, for example by use of a Braun dismembrator, by a French press or by mortaring of lyophilized mycelium followed by extraction in buffer (preferably of low ionic strength such as 1–50 mM Tris). After separating the liquid from the solid matter, nucleic acid was removed, for instance by compounds such as streptomycin sulphate, Polymin B or protamine sulphate. Protein in the liquid phase was precipitated using, for example, ammonium sulphate, pH 8.0. The precipitate forming between 50%–80% saturation was collected then dissolved and active fractions containing the enzyme system were collected. After fractionation of these active fractions by molecular sieving techniques (for example, low pressure resins, AcA54 or Sephadex G75, which fractionate approximately between 3 and 80 kDalton range) the activity disappeared. Only after combining fractions eluting early from these columns with fractions eluting later, were fractions containing the HMW and LMW components identified using the DTNB assay.

The HMW and LMW components of the enzyme system were individually purified. The fractions containing the HMW component were further fractionated using anion exchange resins such as diethylamino ethyl (DEAE) or mono Q at low, medium or high pressure, for example TSK-DEAE-650, equilibrated with a low ionic strength buffer (for example 50 mM Tris-HCl pH 8.0, 1 mM EDTA). The HMW component was eluted with a salt gradient, for example ranging from 0–0.5M NaCl. Fractions showing activity in the DTNB assay eluted between 0.2 and 0.4M NaCl with this gradient. After this step the HMW component was separated from the enzyme glutathione reductase which elutes at low concentrations. The pooled fractions were further purified by affinity chromatography resins having affinity for $NAD^+$ or $NADP^+$, such as Blue Sepharose CL-6B. The resin was washed by a low ionic strength buffer of pH below 7.3, for example 20 mM Tris, 1 mM EDTA. The HMW component was eluted from the resin by adding 5 mM NADPH to the same buffer.

The fractions of the molecular sieving column which contain the LMW component were further purified using anion exchange resins such as DEAE or mono Q at low, medium or high pressure, for example TSK-DEAE-650S, equilibrated with a low ionic strength buffer, preferably 10 mM Tris-HCl pH 8.0, 1 mM EDTA or lower. The LMW component was eluted with a salt gradient, for example ranging from 0–0.3M NaCl. To stabilize the activity of the LMW component, the fractions containing this component received a reducing agent, for instance DTT or β-mercaptoethanol.

Before testing of the activity the reducing agent was always removed, for instance by extensive washing of the LMW component bound to a DEAE resin, by gel filtration, or by dialysis of the eluted fractions against a low ionic strength buffer such as 1–40 mM sodium acetate. The LMW component was further purified using cation exchange resins such as carboxymethyl (CM—)Sepharose equilibrated with a low ionic strength buffer with a pH below 5.5 (for example 20 mM sodium acetate pH 4.9 containing 1 mM EDTA). The LMW component was eluted with a gradient, for example 0–600 mM sodium acetate. Fractions containing the LMW polypeptide eluted between 250 and 450 mM acetate. The purity of the HMW and LMW component was examined by SDS-PAGE. Amino acid sequencing of these bands showed that these polypeptides were substantially free of cellular debris and other microorganism proteins, as judged by SDS-PAGE followed by amino acid sequencing.

After Blue Sepharose CL-6B affinity chromatography the HMW component has a specific activity in the range of 1.0–2.0 µmoles NADPH/min/mg prot. as determined with DTNB as a substrate and a fixed amount of DEAE purified LMW component. After CM-Sepharose chromatography the LMW component has a specific activity of 0.3–0.4 µmoles NADPH/min/mg prot. as determined with DTNB as a substrate. However, the measurement of specific activity is very dependent on the degree of purity of the HMW and LMW components, the amount of time that has elapsed after purification when the assay is conducted, and on the relative amounts of HMW and LMW components added to the reaction mixture. The highly purified polypeptide components are less stable than the partially purified polypeptide components.

The enzyme system was able to reduce low molecular weight disulphides such as bis-ACV, DTNB, bis-(cys-gly) and bis-(Coenzyme A). Michaelis Menten constants ($K_M$) were measured for these substrates, using HMW and LMW components obtained after DEAE chromatography (18 and 2.5 µg, respectively). The $K_M$ values were on the order of 125 µM for bisACV, 1.4 µM for DTNB, 83 µM for bis-(Coenzyme A) and 800 µM for bis-(cys-gly). The enzyme system was also able to reduce protein disulphides such as the disulphide in insulin. The $K_M$ value for insulin, based on the molecular weight of the native molecule which contains three disulphides, is 2.3 mM.

Amino acid sequences of the HMW and LMW components isolated from *P. chrysogenum* were determined by methods known in the art. The HMW gene product comprises the amino acid sequence:

Met—Val—His—Ser—Lys—Val—Val—Ile—Ile—Gly—Ser—Gly—Pro—Gly—Ala—His—Thr—Ala—Ala—Ile—Tyr—Leu—Ser—Arg—Ala—Glu—Leu—Gln—Pro—Val—Leu—Tyr—Glu—Gly—Met—Leu [SEQ ID NO:2].

Residues 2–29 have been determined by amino acid sequence analysis of the purified protein. Nucleotide sequence data of the cloned HMW gene confirmed tentative assignments in this sequence and extended the sequence with residue 1 and residues 30–36.

Some of the amino acids could not be assigned beyond a reasonable doubt; these tentative assignments are given in parentheses. The LMW gene product comprises the amino acid sequence:

(Gly)—Val—Thr—Pro—Ile—Lys—Ser—Val—Ala—Glu—Tyr—Lys—Glu—Lys—Val—Thr—Asp—Ala—(Thr)—(Gly)—Pro—Val—(Val)—(Val)—Asp—Phe—His—Ala—Thr—(Trp)—(Glu)—Gly—Pro—(Xaa)—(Lys)—(Ala)—(Ile)—(Ala)—(Pro)—(Glu) [SEQ ID NO:3].

The invention also includes polypeptides with different amino acid sequences which are homologous to the HMW and LMW polypeptides of *P. chrysogenum* or parts thereof and show a comparable activity. Homology is defined herein as a similarity score of at least 80% when compared to the amino acid sequence of the HMW or LMW protein, as determined by the BestFit program of the Wisconsin Sequence Analysis Software Package (version 6.0, release 1989, GCG, University of Wisconsin, U.S.A.) using parameter settings gap weight 3.000 and length weight 0.100. Amino acid sequences with similarity scores less than 85% but higher than 60% are termed similar herein. Homologous proteins may be isolated from natural sources, or may be produced by mutagenesis of the HMW and LMW encoding genes.

Comparison of the amino acid sequence with known amino acid sequences revealed that the N-terminal amino acid sequence of the HMW polypeptide is similar to the N-terminal amino acid sequence of thioredoxin reductase of *E. coli* (EC 1.6.4.5) (84% similarity in a 33 amino acid overlap). The LMW sequence may contain the highly conserved redox sequence Cys-Gly-Pro-Cys [SEQ ID NO:5] typical for thioredoxins and may be similar to thioredoxins obtained from several organisms (60% similarity in a 38 amino acid overlap to thioredoxin of *E. coli*). The finding that the LMW component could be replaced by thioredoxin obtained from *Spirulina platensis*, in an assay in which either DTNB or bis-ACV were reduced by the combined action of HMW and LMW component and NADPH, further indicates the homology of the LMW component with thioredoxin. Thus it is highly probable that the high molecular weight polypeptide and the low molecular weight polypeptide isolated from *P. chrysogenum* can be referred to as the thioredoxin reductase and the thioredoxin of *P. chrysogenum*, respectively. The polypeptides or parts thereof may be joined to other compounds, such as antigens, receptors, labels or the like.

Also provided for in this invention are the genes encoding the polypeptide components of the oxido reductase system of *P. chrysogenum*. The N-terminal amino acid sequences of the two polypeptides have been determined. This enables, using the approach of reverse genetics defined herein below, the isolation of genes which encode these polypeptides, and subsequently the determination of the nucleotide sequences of these genes (Miller and Ingolia, supra). In the reverse genetics approach, oligonucleotide probes are designed based on a partial amino acid sequence from the N-terminus or internal peptide fragments of the purified enzyme (see, for example, Maniatis et al., *Molecular Cloning* (2nd ed.) 1989). These oligonucleotide probes may be used directly to screen genomic or cDNA libraries for the gene of interest. An example of such a library, containing DNA fragments of *P. chrysogenum* is the lambda phage vector EMBL-3 which has been described in EP 0354624. Alternatively, a set of synthetic oligonucleotide probes may be designed to be used in a polymerase chain reaction (PCR) using genomic DNA, cDNA or mRNA from the microorganism of interest to generate a larger probe fragment.

In another approach antibodies raised to the purified enzyme, or parts thereof, may be used to screen expression libraries for the gene of interest. Once genes, or part of the genes encoding the NMW and LMW polypeptides have been cloned, these genes can be used as probes to isolate the corresponding genes from other organisms by heterologous hybridization. These probes can be restriction fragments derived from DNA isolated from, for example, *P. chrysogenum*. Alternatively, synthetic oligonucleotide probes can be made for instance comprising a region of the most conserved sequences in the gene. These oligonucleotide sequences can be used for screening of genomic or cDNA libraries. On the other hand, oligonucleotides may be made which can be used to isolate the gene of interest, or part of it, from genomic DNA, cDNA or mRNA of the microorganism of choice by using the PCR technique.

In yet another approach, cloned sequences of the genes encoding the HMW and LMW polypeptides may be used to create oxido reductase mutants by gene disruption of the authentic HMW and LMW polypeptide encoding genes by transformation with cloned mutant derivatives of these genes. The resulting thioredoxin or thioredoxin reductase mutant can subsequently be used as a host for the selection and isolation of DNA fragments from the same or another organism which is able to restore oxido reductase activity.

Probes may be modified by conjugation with a variety of labels which allow for detection of duplex formation between the probe and its complementary target. Labels include radioactive isotopes, ligands, e.g., biotin, enzymes, fluorescers and the like. A wide variety of protocols for labelling probes and detecting duplexes formed between probes and their target hybridization sequences have been described in the literature. See, for example, Berger and Kimmel, editors, *Guide to Molecular Cloning Techniques* (1987), Academic Press Inc., San Diego, Calif. Probe sequences may also be joined to a variety of other nucleic acid sequences. Among these other nucleic acid sequences are vectors such as plasmids, cosmids, phages, and the like. By joining the probe sequence to a vector sequence, probes may be conveniently created, expanded, stored, and modified.

Convenient restriction sites may be designed into the DNA sequences encoding the enzyme system; when possible, the restriction site(s) leave(s) the amino acid sequence of the expression product unaltered. In some cases, incorporation of new restriction sites may yield an altered amino acid sequence. However, it is highly desirable that the three-dimensional structure of the HMW and LMW polypeptides be retained, particularly that (those) portion(s) of the structure of the enzyme system which may be responsible for enzyme activity.

The invention also includes genes comprising different nucleotide sequences, for instance with conservative mutations, where the sequence encodes the same amino acid sequence, but may have as many as 30% different bases, more usually not more than 10% different bases, or mutations which are non-conservative, where fewer than about 10%, more usually fewer than about 5%, and preferably not more than 1% of the amino acids are substituted or deleted, and there are fewer than 5% of inserted amino acids, where the percent is based on the number of naturally occurring amino acids. Said genes may also be isolated by hybridization.

Once having isolated a DNA sequence encoding the enzyme system, the DNA sequence may then be used for expression in a convenient host, either prokaryotic or eukaryotic. For expression of the sequence, where necessary an initial methionine codon is provided. Where the DNA sequence encoding the enzyme system is to be expressed in a host which recognizes efficiently the authentic transcriptional and translational regulatory regions of the native enzyme system encoding gene(s), the entire gene(s) with its authentic 5' and 3'-regulatory regions may be introduced into the host without further manipulation. Where the DNA sequence encoding the enzyme system is to be expressed in a host cell which does not recognize the authentic expression signals or where the native gene encoding the enzyme system is not being used, further manipulation may be required. The non-coding 5'-region upstream from the open reading frame (ORF) may be removed by exonuclease digestion, for instance by Bal31 digestion, or the like. Alternatively, where a convenient restriction site is present near the 5'-terminus of the ORF, the DNA may be restricted and an adapter employed for linking the ORF to a DNA sequence providing for expression of the ORF in the host cell, where the adapter provides for the lost nucleotides of the ORF. Similarly the authentic 3'-transcriptional regulatory regions can be replaced by 3'-transcriptional regulatory regions functional in the host. In addition, the expression in other hosts, especially prokaryotic ones, may require the removal of introns in the gene, or the use of cDNA copies of the gene.

For the genes encoding the component polypeptides of the enzyme system, the original expression signals can be replaced by expression signals obtained from the same or another organism, which are functional in the host cell, for example, in *E. coli* or in Streptomyces, or in filamentous fungi such as *P. chrysogenum*. These promoters preferably are expressed during β-lactam synthesis. Expression signals are defined herein as signals necessary and sufficient for efficient initiation and termination of transcription and efficient initiation and termination of translation.

The genes may be introduced into the host cell in accordance with known techniques, such as transformation, transfection by contacting the cells with a virus, microinjection of the genes into the cells and the like. The genes can be incorporated in constructs, either together in one construct, or each in a separate construct. The genes can be introduced into strains of *P. chrysogenum* or other β-lactam producing organisms, preferably production strains, by (co) transformation with a suitable selection marker. Those skilled in the art would know that selection of transformants can be achieved by using different selection markers, homologous or heterologous to the host, in the presence or absence of vector sequences, physically linked or not to the non-selectable DNA as suitable. Particularly, the microbial hosts are selected from the group of fungi, preferably *Penicillium chrysogenum*, *Acremonium chrysogenum* or *Aspergillus nidulans*, or from the group of Streptomyces.

In use for β-lactam production the isolated enzyme system of *P. chrysogenum* finds several applications. Next to the polypeptide components of the *P. chrysogenum* system, also thioredoxin and thioredoxin reductase obtained from other organisms can be used. This is exemplified by the finding that the LMW component can be replaced by thioredoxin obtained from *Spirulina platensis*, in an assay in which either DTNB or bis-ACV are reduced by the combined action of HMW and LMW components and NADPH. Thioredoxin is defined as a protein with two redox-active half cystine residues in an exposed active center, having the amino acid sequence: -Cys-Gly-Pro-Cys-, and which is able to reduce, besides other compounds containing disulphide bonds, disulphide bonds in proteins (A. Holmgren, *Ann. Rev. Biochem.* (1985) 54:237–271). The polypeptide components do not have to be purified completely; for most applications partially purified polypeptide components can be used.

The enzyme system can replace DTT. DTT is used to provide reducing conditions, for instance in processes where isolated enzymes are used to produce β-lactam compounds. The activity of most of the β-lactam biosynthetic enzymes is stimulated by the presence of DTT. The tripeptide ACV, the substrate of IPNS, has to be in a reduced state as well. However, in the presence of iron DTT will inactivate many enzymes (Kim et al., *J. Biol. Chem.* (1985) 260:15394–15397). Iron is an essential cofactor for the enzymes involved in β-lactam synthesis, such as catalyzing ring closure, ring expansion and hydroxylation. It has been exemplified that the thioredoxin system can replace DTT to provide reducing conditions for β-lactam biosynthesis. In the presence of the oxido reductase system obtainable from *P. chrysogenum* and the thioredoxin systems already known, isopenicillin N was produced from ACV disulphide under non-reducing conditions.

The LMW component of all those enzyme systems can be used to enhance the activity of β-lactam biosynthetic enzymes which are dependent on the stimulating effect of DTT. This has been exemplified for ACVS. Addition of thioredoxin and DTT to the enzyme resulted in higher activity than the addition of DTT alone. Thioredoxin reductase is defined as a protein which is able to reduce thioredoxin in the presence of a suitable electron donor.

Thus a process for reducing disulphide compounds and compounds involved in the production of β-lactam derivatives in vitro has been provided for by contacting, in the presence of an electron donor, the compounds to be reduced with a composition comprising the oxido reductase system or components, wherein said enzyme system is obtainable from *P. chrysogenum*, and has as components a high molecular weight (HMW) polypeptide with a molecular weight of about 36 kDa and a low molecular weight (LMW) polypeptide with a molecular weight of about 12 kDa, and being capable of reducing disulphide compounds, or with a LMW polypeptide in the presence of a reducing agent as for instance DTT, or wherein said enzyme system or components are a thioredoxin system, or thioredoxin and a thioredoxin reductase, obtainable from any organism.

In use, the genes encoding up to the entire sequence of the polypeptide components of the oxido reductase system of *P. chrysogenum* find several applications. Rather than isolate the enzyme system from natural sources, the HMW and/or LMW components may be prepared from microorganisms modified by recombinant techniques. This may be accomplished by preparing a DNA construct comprising one or more genes encoding up to the entire sequence of the HMW and/or the LMW polypeptide component of the oxido reductase system wherein optionally one or both of the expression signals has been replaced by expression signals obtained from the same or another organism, as described above; and transforming a host organism with these DNA constructs. The enzyme system or components thereof may be isolated from transformed hosts essentially according to methods provided above.

By use of cloned HMW and LMW genes or cloned genes encoding thioredoxin and thioredoxin reductase, modified enzymes may be designed and synthesized. The DNA of the invention may also be modified by known techniques of site-directed mutagenesis to yield DNA in which specific mutations, deletions and insertions have been introduced. These modifications will result in modified characteristics of the enzymes, such as a change in pH or temperature optimum, a change in stability or a change in substrate specificity. The latter could, for instance, result in an enzyme with a higher affinity for other components of the oxido reductase system, for β-lactam biosynthetic enzymes or for disulphide compounds, for instance ACV, involved in the production of β-lactam compounds, or a combination thereof. The host strains, transformed with genes encoding these modified enzymes, may be able to produce β-lactam antibiotics at higher levels as compared to non-transformed strains.

The genes encoding the polypeptide components of all thioredoxin systems including the oxido reductase system of *P. chrysogenum* may be used for enhancing the production of β-lactam compounds in a microbial host. DNA constructs prepared as described in this invention are used to transform microorganisms producing said compounds. Preferred microorganisms for transformation are eukaryotic β-lactam producers such as *P. chrysogenum*, *A. chrysogenum* or *Aspergillus* species, and prokaryotic β-lactam producers such as Flavobacterium or Streptomyces species.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

11

The following non-limitative examples will further illustrate the invention.

EXPERIMENTAL

EXAMPLE 1

Demonstration of DTNB Reducing Activity by Combining High and a Low Molecular Weight Fraction of Extracts of *Penicillium chrysogenum*

Culturing:

Rice containing spores of *P. chrysogenum* strain NRRL 1951 was prepared as described by Lein et al. (Lein (1986) in Vanek and Hostalek (ed.) Buttersworth, Boston, pp. 105–139, Overproduction of microbial metabolites: strain improvement and process control strategies). Tryptic soy broth (TSB) with 1% starch as the carbon source was inoculated with 105 conidia per ml. After growing for 24–48 h at 30° C., 5 ml of this culture were used to inoculate 500 ml of TSB-starch medium. After 24 h, the mycelia were harvested by filtration and the resulting filter cake was washed twice with 0.9% NaCl. Packed mycelia were kept frozen at −20° C. until use.

DTNB reductase activity assay:

DTNB reductase activity was measured as follows: The reaction mixture contained (final concentration) 50 mM Tris-HCl pH 8.0, 1 mM EDTA, 0.02 mM DTNB, 0.2 mM NADPH. Enzyme preparations were added to a final volume of 1 ml. The reaction was followed by measuring the increase of absorbance at 412 nm at 25° C. during the first three minutes or longer if necessary. Control experiments were included in which the enzyme preparations or NADPH were omitted.

Preparation of cell fractions:

10 g (wet weight) of mycelia were suspended in 0.05M Tris-HCl buffer pH 8.0, 1 mM EDTA (TE-buffer) to a total volume of 50 ml and disrupted in a Braun dismembrator (Braun, Melsungen, FRG) using Ballotini glass beads (Sigma type V, diameter 450–500 μm) for periods of 30 s at intervals of 15 s with refrigeration. The homogenized suspension then was cleared by passing over a glass wool filter. This step and the following ones were carried out at 4° C. To the cell-free extract, 10% (w/v) streptomycin sulphate in TE-buffer was added slowly to a final concentration of 1%. After stirring for 45 min in the cold, the nucleic acid precipitate was removed by centrifugation at 10,000+g for 10 min. The supernatant was fractionated by precipitation with ammonium sulphate while maintaining the pH of the solution at 8.0 during ammonium sulphate additions. The fraction precipitating between 50–80% saturation was dissolved in a small volume of TE-buffer. The dissolved fraction was applied to an AcA54 gel-filtration column (2.6×35 cm) equilibrated with TE-buffer. The column was eluted with TE-buffer at a flow rate of 0.5 ml/min and fractions of 3 ml were collected.

DTNB reductase activity was present in the ammonium sulphate pellet precipitating between 50–80% saturation, but was absent in the separate fraction from the AcA54 gel-filtration column. DTNB reductase activity was restored by adding particular fractions containing LMW material (<15 kDa) to particular fractions containing HMW material (>15 kDa). The DTNB reductase activity was found to be dependent on the presence of NADPH. It can be concluded from these experiments that DTNB reduction by cell-free extracts of *P. chrysogenum* is achieved by at least two polypeptide components (HMW and LMW components) and an electron donor.

12

EXAMPLE 2

Purification of the HMW and LMW Components of the Oxido Reductase System Involved in the Reduction of DTNB DTNB reductase activity assay:

The assay condiitions for the purification of the HMW component were as described in Example 1. The reaction mixture was prepared as follows. For the purification of the HMW component, 50–100 μl AcA54 gel-filtration fractions containing LMW material (<15 kDa) were included. For the purification of the LMW component, 25–50 μl of gel-filtration fractions containing HMW material (>15 kDa) were included in the mixture.

Purification of the HMW component; Gel-filtration fractions which contained HMW material and which were active in the DTNB assay were pooled and applied to a TSK-DEAE-650 (Merck) column (10 ml bed volume) which was previously equilibrated with TE-buffer. The column was eluted with a linear gradient of 0 to 0.5M NaCl. Fractions eluting at 0.25 to 0.32M NaCl were active in the DTNB reductase assay. These fractions were subsequently loaded on a Blue Sepharose CL-6B column. Fractions containing HMW were eluted with 5 mM NADPH in 20 mM Tris-HCl buffer pH 7.25 containing 1 mM EDTA. This procedure resulted in a fraction containing one polypeptide band with an apparent molecular mass of 36 kDa as determined by SDS-PAGE (Laemmli, *Nature* (1970) 227:680–685).

Purification of the LMW component:

Gel-filtration fractions which contained LMW material and which were active in the DTNB reductase assay were pooled, incubated with 2 mM DTT and applied to a TSK-DEAE-650S) (Merck) column with 10 ml bed volume, which was previously equilibrated with 10 mM TE-buffer. The column was eluted with a linear gradient of 0–0.3M NaCl. Fractions eluting at 0.1 to 0.15M NaCl were active in the DTNB reductase assay. These fractions were incubated with 2 mM DTT for 30 min. After dialysis against 20 mM sodium acetate buffer pH 4.9 containing 1 mM EDTA, the combined fractions were loaded on CM-Sepharose, 10 ml bed volume, equilibrated in the same buffer. The column was eluted with a linear gradient of 40–600 mM sodium acetate in the same buffer. Fractions eluting between 300–400 mM acetate buffer were active in the DTNB reductase assay. This procedure resulted in a fraction containing a polypeptide band with an apparent molecular mass of 12 kDa as determined by SDS-PAGE.

EXAMPLE 3

Determination of Amino Acid Sequences of the Purified HMW and LMW Components

The purified LMW component was applied to a 17.5% SDS-PAA gel, the purified HMW component to a 12% SDS-PAA gel. After running of the gels, the polypeptides were electrophoretically transferred to a polyvinylidene difluoride membrane. The membrane was stained with 0.1% Coomassie Brilliant Blue R250 in 50% methanol, 10% acetic acid in water and subsequently destained. The polypeptide bands corresponding to the HMW and the LMW component were analyzed for N-terminal amino acid sequencing, using a gas phase sequenator (Applied Biosystems model 470 a).

The following amino acid sequence was determined for the HMW polypeptide:

(Val)—(His)—Ser—Lys—Val—Val—Ile—Ile—Gly—Ser—Gly—Pro—Gly—Ala—His—Thr—Ala—Ala—
Ile—Tyr—Leu—Ser—(Arg)—Ala—Glu—Leu—Gln—Pro [SEQ ID NO:11].

Tentative assignments are given in parenthesis.
The following amino acid sequence was determined for the LMW polypeptide:

(Gly)—Val—Thr—Pro—Ile—Lys—Ser—Val—Ala—Glu—Tyr—Lys—Glu—Lys—Val—Thr—Asp—Ala—
(Thr)—(Gly)—Pro—Val—(Val)—(Val)—Asp—Phe—His—Ala—Thr—(Trp)—(Glu)—Gly—Pro—
(Xaa)—(Lys)—(Ala)—(Ile)—(Ala)—(Pro)—(Glu) [SEQ ID NO:3].

Tentative assignments are given in parentheses.

Comparison of these amino acid sequences with known amino acid sequences and nucleotide sequences can be performed by a library search on the protein databases of the National Biomedical Research Foundation (updated to March 1990) and the Swiss Protein Library (updated to April 1990), and the nucleotide sequence databases of the European Molecular Biology Laboratory (updated to May 1990), using, respectivelyt the FastP and TFastA programs described by Lipman and Pearson (Science (1985) 227:1435–1441) and Pearson and Lipman (Proc. Natl. Acad. Sci. (USA) (1988) 85:2444–2448). A more detailed comparison of the similarity between two sequences can be made by the Bestfit program which uses an algorithm described by Smith and Waterman (Advances in Applied Mathematics, 1981, 2:482–489). The FastP, TFastA and BestFit programs used are part of the GCG Sequence Analysis Software Package (version 6.0, release 1989, GCG, University of Wisconsin, U.S.A.). The search and comparison revealed that the sequence is similar to the N-terminal amino acid sequence of thioredoxin reductase of E. coli (EC 1.6.4.5) (84% similarity in a sequence of 27 amino acids overlap).

No significant similarity is found for the LMW sequence amino acid residues 2–16 in the above-indicated libraries. Therefore, the oxido reductase system having the above sequences and characteristics is a novel system. The extended LMW sequence 16–38 is tentative at several positions. Nevertheless, it was recognized that residues 31–34 form a putative consensus sequence Cys-Gly-Pro-Cys [SEQ ID NO:5], typically involved in redox reactions. A library search and comparison performed with LMW sequence 2–38 confirmed this conclusion by revealing the similarity of this sequence to thioredoxin from different species (for instance 60% similarity in a 38 amino acid overlap with thioredoxin of E. coli).

EXAMPLE 4

Demonstration of the Reduction of bis-ACV by the Combined Action of the HMW and LMW Component Bis-ACV reductase assay;

The reaction mixture contained 50 mM Tris-HCl pH 8.0, 1 mM EDTA, 0.5 mg bis-ACV (Bachem Feinchemikalien AG, Bubendorf, Switzerland), 0.1 mM NADPH and purified HMW and LMW components. The assay volume was 1 ml and incubation was at 30° C. The reaction was followed at 340 nm.

Control experiments were included in which either the HMW or the LMW component, or bis-ACV was omitted. Whereas no activity was found in any of the control experiments, a decrease of absorbance at 340 nm, due to a consumption of NADPH, was observed in reaction mixtures which contained all of the above components.

EXAMPLE 5

Demonstration of the Reduction of bis-ACV and DTNB by the Combined Action of the HMW Component Obtained from P. chrysogenum and Thioredoxin Obtained from Spirulina platensis The DTNB reductase assay was done as described in Example 2, except that both of the HMW and LMW components used were purified until after DEAE chromatography. The amount of protein present in the reaction mixuture was 0.264 mg of the HMW component and either 20 µg of the LMW component or 10 µg of the thioredoxin obtained from Spirulina platensis (Sigma, St. Louis, U.S.A.). In this experiment the increase of absorbance was measured at 412 nm. After 15 minutes of incubation the increase of absorbance was 0.225 for the combination of HMW and LMW, and 0.080 for the combination of HMW and thioredoxin. Control experiments in which either the HMW or the LMW component were omitted, or in which either the HMW or the thioredoxin were omitted, did not show an increase in absorbance.

Reduction of bis-ACV by the combined action of the HMW compound of P. chrysogenum and thioredoxin of Spirulina platensis was determined as follows. The reaction mixture contained 80 mM Tris-HCl pH 8.0, 1.5 mM EDTA, 0.03 mg/ml bis-ACV and 0.1 mM NADPH. The amounts of the proteins added are given in Table 1. The HMW and LMW components were purified until after DEAE chromatography. The assay volume was 0.5 ml and incubation was at room temperature. The reaction was followed at 340 nm and activity was expressed as µmoles of NADPH oxidized per minute.

TABLE 1

| HMW (µg) | LMW (µg) | thioredoxin (µg) | µmol NADPH/minute |
|---|---|---|---|
| 250 | 10 | 0 | 2.25 |
| 250 | 5 | 0 | 1.13 |
| 60 | 0 | 4 | 1.93 |
| 250 | 0 | 2 | 0.64 |
| 250 | 0 | 1 | 0.32 |
| 125 | 0 | 0 | 0.32 |
| 0 | 10 | 0 | 0.16 |
| 0 | 0 | 4 | 0.16 |

The results show that thioredoxin of Spirulina platensis has affinity for the substrate bis-ACV. The activity was clearly dependent on the concentration of thioredoxin used. Moreover, the results show that the HMW component of P. chrysogenum has affinity for thioredoxin obtained from Spirulina platensis.

EXAMPLE 6

Demonstration of the Production of Isopenicillin N from bis-ACV Under Non-reducing Conditions The enzymatic synthesis of isopenicillin N is dependent on the presence of the thiol form of ACV. In this example the synthesis of isopenicillin N by IPNS was performed with bisACV as a substrate. The assay conditions for the production of isopenicillin N were as follows. The reaction mixture contained 50 mM Tris-HCl pH 7.5, 1.42 mM bis-ACV, 3.84 mM Ascorbate, 0.8 mM $Fe^{2+}$, 0.7 mM EDTA, 14.28 mM NADPH, 16.8 µg of IPNS and HMW and LMW components as required. Enzyme preparations were added to a final volume of 70 µl. The IPNS was a preparation made from an *E. coli* strain expressing the IPNS gene from *Flavobacterium sp.* 12.154. The IPNS gene has been cloned into the PIN OMPA expression vector (F. M. Ausubel et al. (eds, *Current Protocols in Molecular Biology* (1987–1988), John Wiley and Son, New York). *E. coli*MC1022 has been transformed with the resulting vector pDS510. *E. coli*MC1022 containing pDS510 was grown in LB medium+50 µg/ml kanamycin overnight. The cells were diluted 100 fold into LB+50 µg/ml kanamycin+0.1 mM isopropylthiogalactoside (IPTG), and grown in 2 liter flasks. The cells were harvested after 6 hours; the OD 600 was approximately 2. The cells were collected by centrifugation and washed in 50 mM Tris-HCl, pH 7.5. The cells were sonicated in the same Tris buffer containing 1 mM DTT. The crude extract was treated with 1% streptomycin sulphate to precipitate nucleic acids. An ammonium sulphate fraction precipitating between 40–80% saturation was collected. The sample was run on an AcA44 column (55 cm×2.6 cm), at 0.33 ml/min, 12 min. Antibiotic activity in the fractions was assayed in the standard bioassay employing *Micrococcus luteus* as the test organism. A standard curve of different cephalosporin C concentrations was formed, thus the numbers express activity relative to that of cephalosporin C. Active fractions were pooled and loaded on a DEAE-Sepharose column 1.6 cm×10 cm. Proteins were eluted with a 150 ml gradient of 0 to 400 mM NaCl. The flow was 0.33 ml/min. Fractions were collected every 7.5 min. The fractions were assayed and fractions showing high activity were pooled. This IPNS preparation was used for further experiments. The HMW and LMW components were partially purified including DEAE chromatography as described in Example 2.

The formation of isopenicillin N from bis-ACV in the presence of the oxido reductase system from *P. chrysogenum* was determined. Antibiotic activity was determined as described above. Control experiments were included in which either the HMW or the LMW component or NADPH was omitted. The results of a typical experiment were as follows.

| Production of isopenicillin N from bis-ACV under non-reducing conditions | | | | |
|---|---|---|---|---|
| HMW µg/reaction | LMW µg/reaction | NADPH | Zone ofinhib. mm | Antibiotic µg/ml |
| 6.6 | 8 | – | ND | ND |
| 39.6 | 8 | – | ND | ND |
| 145.2 | 11 | – | ND | ND |
| – | 8 | + | ND | ND |
| – | 11 | + | ND | ND |
| 6.6 | – | + | ND | ND |
| 39.8 | – | + | ND | ND |
| 105.6 | – | + | ND | ND |
| 145.2 | – | + | ND | ND |
| 6.6 | 8 | + | 7 | 38 |
| 19.8 | 8 | + | 12 | 72 |
| 39.6 | 8 | + | ND | ND |
| 105.6 | 8 | + | ND | ND |
| 145.2 | 11 | + | ND | ND |

The production of antibiotic was not detected in any of the control experiments. When both the HMW and the LMW components and NADPH were present, antibiotic activity was detected. The synthesis of isopenicillin N appeared to be inhibited by high concentrations of the HMW component which may be due to impurities in the preparation.

This example demonstrates that the oxido reductase system of *P. chrysogenum* provides the reducing environment necessary for the production of isopenicillin N from bis-ACV by IPNS.

EXAMPLE 7

Demonstration of Enhanced Activity of ACVS by Contacting with the LMW Component

Purification of ACVS:

ACVS was purified from *Acremonium chrysogenum* C10 (ATCC 48272) as essentially described by Baldwin et al. (*J. Antibiotics* (1991) 44:241–248). The ammonium sulphate precipitate was dissolved and applied onto a gel-filtration column (Ultrogel AcA34). The ACVS activity assay was done as described by Van Liempt et al. (*J. Biol. Chem.* (1989) 264:3680–3684). Fractions showing high activity of ACVS were collected (75–85 µg protein/ml). The preparation shows a purity of 80% for ACVS as judged after SDS-PAGE and staining with Coomassie Brilliant Blue R250. DTE was removed by passing the enzyme through a PD10 column just before use of the enzyme in further experiments.

Purification of the LMW component:

The LMW component was obtained from *P. chrysogenum* strain Wisconsin 54–1255 (ATCC 28089). The LMW component was purified as described in Example 2. The fractions obtained after DEAE chromatography which were active in the DTNB assay, were used for further experiments.

Determination of ACVS activity in the presence of DTT and LMW component:

The ACVS activity of a reaction mixture containing ACVS and fresh DTT was compared to the activity of a reaction mixture containing ACVS, fresh DTT and the LMW component. As a control for ACVS activity ATP was omitted from the reaction mixture. To compensate for lower protein concentrations in the reaction mixture bovin serum albumin (BSA) was added.

The reaction mixture contained 150 µl of the ACVS preparation. DTT was added to a final concentration of 1.7 mM. ATP was added optionally to a final concentration of 5 mM. Either 25 µl of 0.5 µg/ml BSA solution or 12.5 pl of the same solution together with 12.5 µl of a 1.5 µg/ml LMW component preparation was added. The reaction mixture was allowed to stand for 10 min at room temperature. The reaction was started by the addition of 50 µl of a mixture containing L-α-aminoadipic acid (final concentration 1.3 mM), L-cysteine (1.3 mM), $MgCl_2$ (25 mM), Tris-HCl (350 mM) pH 7.5, EDTA (0.1 mM), glycerol (9% w/w) and 0.25 µCi L-[U-14$_c$]valine (3 µM). The reaction was allowed to proceed for 30 min at 30° C. The reaction was stopped by the addition of 250 pl of a stop mixture (80 UM ACV, 0.3 mM DTT, 0.5 mM L-valine and 10% trichloroacetic acid (TCA)). After separation of the labelled valine by a passage through Pora pak Q (Waters Associated Inc. Milford, Mass.), the dpm-values given below correspond to the ACV produced during incubation. The results are given in Table 2.

| ATP | DTT | LMW | dpm |
|-----|-----|-----|-----|
| −   | −   | −   | 180 |
| +   | −   | −   | 198 |
| +   | +   | −   | 278 |
| +   | +   | +   | 509 |

Similar experiments with LMW component derived from a gel filtration through Ultrogel AcA54 containing no salt showed an even stronger effect on ACVS activity (2.3 fold stimulation). Thus the LMW component stimulates ACVS activity.

EXAMPLE 8

Isolation of the Gene Encoding the HMW Polypeptide

Based upon the N-terminal amino acid sequence of the HMW polypeptide a 29-mer oligonucleotide probe has been synthesized with the following mixed nucleotide sequence:

```
5'-GGA CCI GGA GCI CAC ACI GCI GCI ATC GC-3' [SEQ ID NO:4]
        C       C   G           T
        T   T
``` where A is deoxyadenyl, G is deoxyguanyl, C is deoxycytidyl, T is deoxythymidyl and I is deoxyinosityl.

The rationale for designing deoxyinosityl containing probes is twofold: to expand the number of sequences in the probe to cover all possible codon usages, and to restrict the number of different sequences in the mixture to a reasonable one. Deoxyinosityl itself is considered to be essentially neutral in its effects on forming DNA hybrids.

The techniques and procedures employed in the following process of isolation of the HMW gene are well known in the art and have been adequately described by Maniatis et al. (supra).

The HMW oligonucleotide probe was labelled with gamma[32p]-ATP and T4 polynucleotide kinase. The labelled probe was used to screen a genomic library of *P. chrysogenum*, made in lambda phage vector EMBL-3. Plaque hybridization was performed on approximately $10^4$ plaques on nitrocellulose filters. Hybridization was performed at 42° C. in a standard hybridization solution containing 15% formamide. Filters were washed with 1–2×SSC (1×SSC is: 0.15M sodium chloride/15 mM sodium citrate) at 50°–60° C. In these experiments eight positively responding plaques were found. Five of these were chosen for a second round of screening with the same HMW probe. All five phage isolates gave a clear positive response. Well separated strongly responding plaques were picked for further characterization. Small scale DNA preparations of the recombinant phage were made for each isolate.

Purified DNAs were digested with restriction enzymes and, following agarose gel electrophoresis, Southern blots were prepared according to procedures well known in the art (Maniatis et al., 1989, supra). Hybridization of Southern blots with the HMW probe revealed, for all five lambda phage, positive hybridization of the probe to a unique restriction fragment; SalI restriction fragments sized 4.7 kilobases (kb), 8.0 kb and 6.2 kb derived from lambda phage 1, 4 and 5, respectively, were isolated and subcloned into *E. coli* vector pUC19 (Pouwels et al., *Cloning Vectors A Laboratory Manual*, Elsevier, Amsterdam, 1987). The resulting plasmids, termed pPCH-1, pPCH-4 and pPCH-5, respectively, have been further analyzed by restriction enzyme analysis and Southern blot hybridization. All three plasmids contained a 1.2 kb EcoRV restriction fragment responding to the HMW probe. A partial restriction map of the 4.7 kb SalI fragment contained in pPCH-1 is shown in FIG. 1. A 0.5 kb HindIII-BamHI restriction fragment was identified in pPCH-1, responding to the HMW probe. This fragment was isolated from pPHC-1 and subcloned into M13 sequence vector M13 mp 18/19 (Pouwels et al., supra). Determination of the nucleotide sequence of the HindIII-BamHI restriction fragment was subsequently performed following the procedure of Sanger (Maniatis et al., 1989, supra). The nucleotide sequence revealed an open reading frame encoding the N-terminal amino acid sequence of the HMW gene (Seq. ID No. 1). The position of the 5'-end of the NMW gene, as well as the direction of the transcription of the gene is indicated (FIG. 1).

Figure 2A:
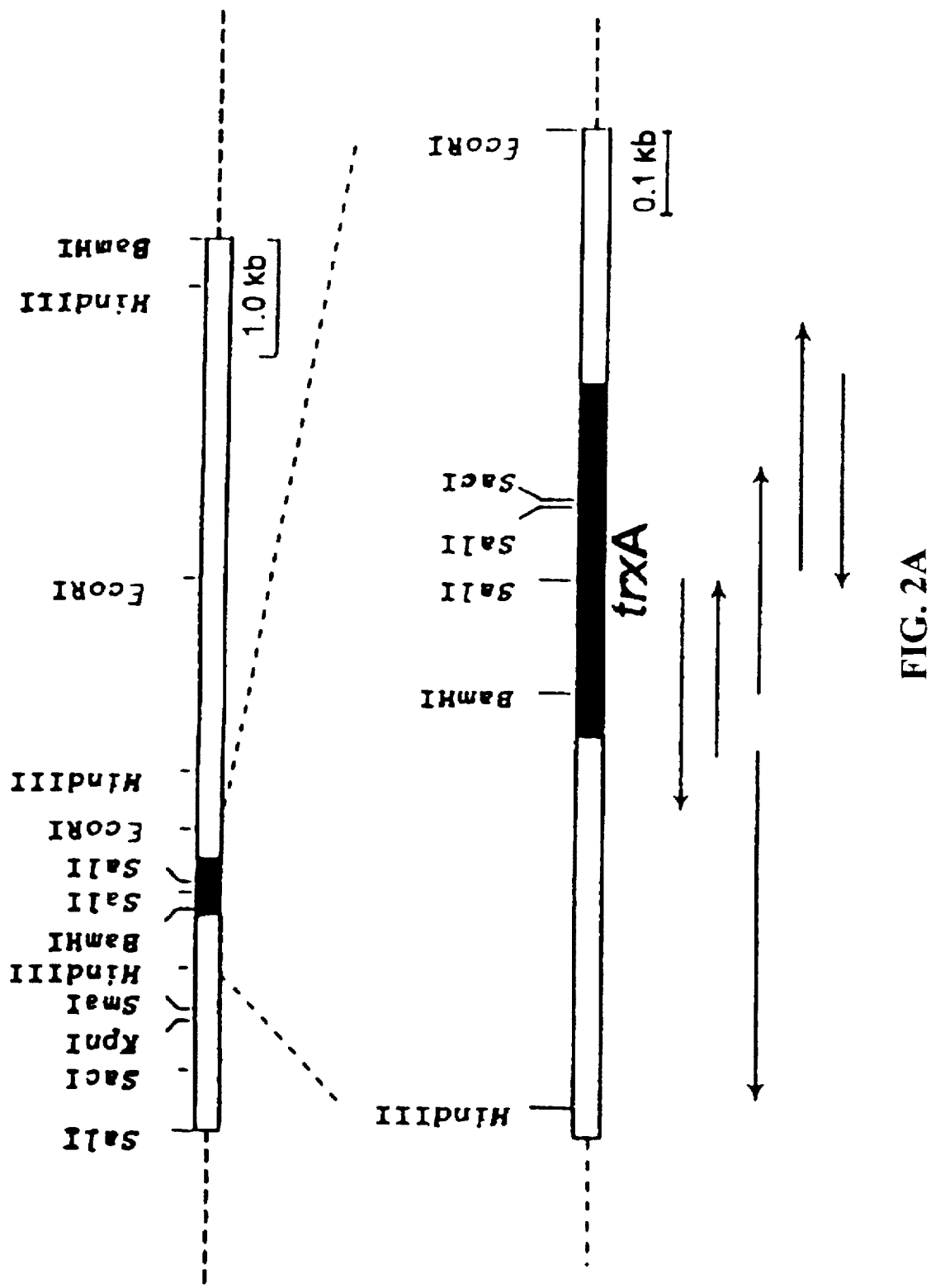
FIG. 2a shows a schematic representation of a partial restriction map of the P. chrysogenum trxA (LMW) gene. Arrows indicate the nucleotide sequence strategy.
Figure 2B:
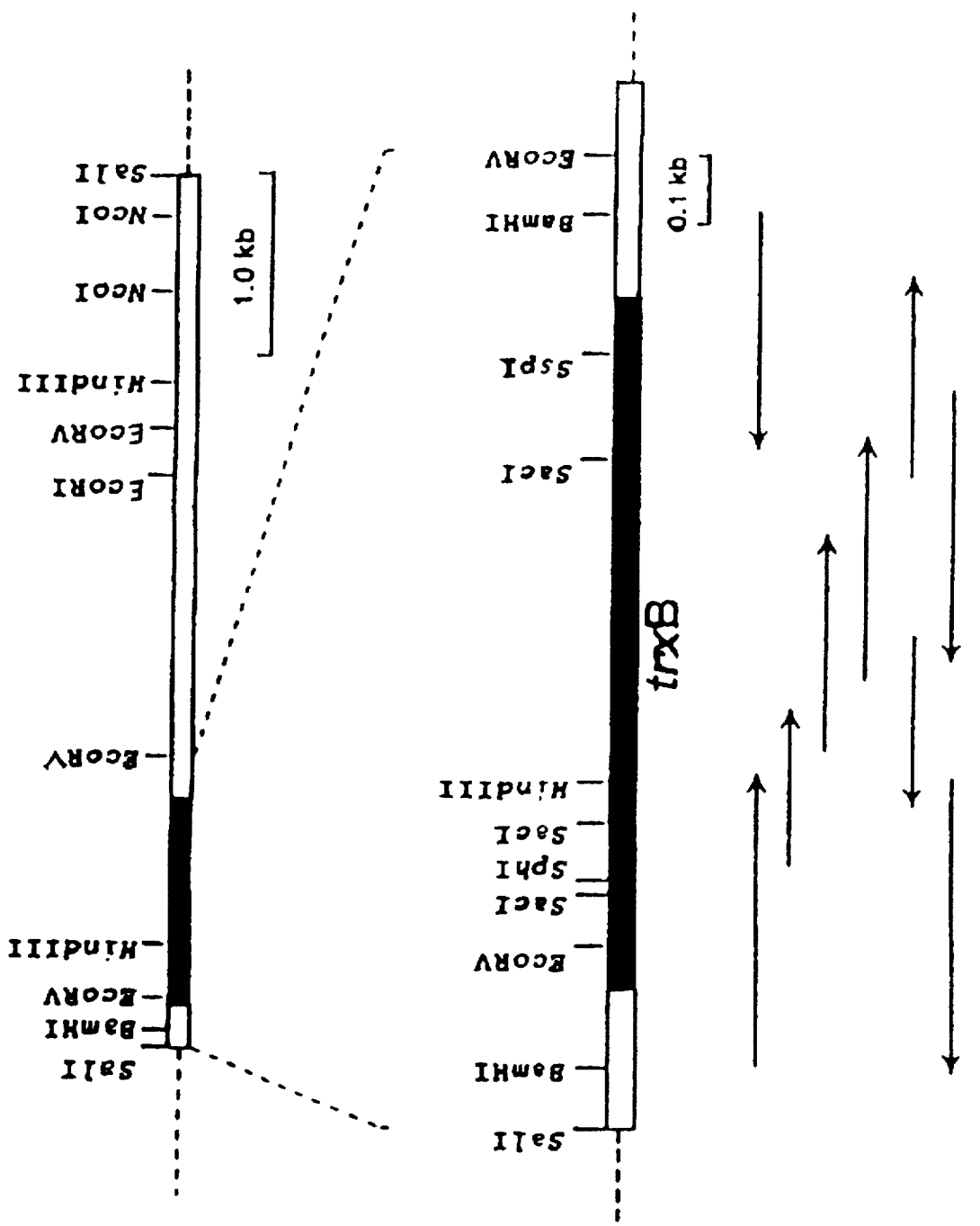
FIG. 2b shows a schematic representation of a partial restriction map of the P. chrysogenum trcB (HMW) gene. Arrows indicate the nucleotide sequence strategy.

The remaining segment of the gene coding for the carboxy-terminal portion of the HMW protein resides in an overlapping 1.3 kb EcoRV fragment. FIG. 2b shows the restriction map of the 1.4 kb BamHI-EcoRV fragment containing the entire HMW reductase gene and the strategy used for sequencing. Seq.ID No. 6 shows the nucleotide sequence of that fragment. It includes 118 nucleotides upstream of the ATG translational initiation codon, 1,150 nucleotides comprising the HMW gene and 153 nucleotides downstream of the chain termination codon. Two introns denoted I and II and possessing 83 and 65 nucleotides, respectively, are located in the amino and carboxy terminal coding parts of the gene, respectively. Consensus fungal intron-exon junction sequences and lariat branch sites are found in each case. The predicted amino acid sequence of the intronless gene codes for a polypeptide of 334 amino acids (including the initiation methionine) (Sequence listing No. 7). The calculated molecular weight of that protein is 35,643 and is in good agreement with that found for the HMW protein from electrophoresis in denaturing gels.

EXAMPLE 9

Isolation and Characterization of the Gene Encoding the LMW Polypeptide

Based upon the N-terminal amino acid sequence of the LMW polypeptide a 29-mer oligonucleotide probe has been synthesized with the following mixed nucleotide sequence:

```
5'-TC IGT IAC TTT TTC TTT GTA TTC IGC IAC-3' [SEQ ID NO:8]
       C   C   C   A   C
``` where A is deoxyadenyl, G is deoxyguanyl, C is deoxycytidyl, T is deoxythymidyl and I is deoxyinosityl (Sequence listing No. 8). Experimental procedures followed are described or referred to in Example 8. Southern analysis of total chromosomal DNA of *p. chrysogenum* with the 29-mer probe identified at low hybridization stringency a 4.0 kb SalI restriction fragment.

The same hybridization conditions were used to screen the AEMBL_3 genomic library and four positively responding recombinant phage plaques were recovered. After purification, the DNA of one phage was found to contain a 0.65 kb SalHindIII fragment that hybridized to the probe and was subcloned into the vector pUC19. The nucleotide sequence of that fragment was determined and found to contain an open reading frame with a deduced amino acid sequence that matched the NH2-terminal portion of the LMW protein but with the LMW initiation methionine removed. In parallel, a 5.8 kb BamHI fragment was subcloned from the same phage and shown by Southern analysis to contain a 0.7 kb BamHI-EcoRI segment that hybridized to the 29-mer probe and whose sequence overlapped with the 0.65 kb SalI-HindIII fragment. FIG. 2a shows the restriction map of the HindIII-HIEcoRI region containing the entire LMW gene and the strategy used for that region. It includes 383 nucleotides upstream of the ATG translational initiation codon, 457 nucleotides comprising the LMW gene and 74 nucleotides downstream of the chain termination codon. The LMW gene contains a single intron of 139 nucleotides located in the $NH_2$-terminal coding part of the gene. It has the consensus intron-exon junction sequences and lariat recognition branch site found in fungal genes.

Other features of this sequence are two promoter-like motifs in the 5'-untranslated region TATAAA at −204 and CCAATT at −350. The predicted amino acid sequence of the intronless gene contains 106 residues [SEQ. ID NO: 10] (including the initiation methionine) with a calculated molecular weight of 11,333 and is in good agreement with that found for the LMW protein from electrophoresis in denaturing gels.

All publications and patent applications mentioned in this specification are indicative of the level of skill of those skilled in the art to which this invention pertains.

All publications and patent applications are herein incorporated by reference to the same extent as if each individual publication or patent application was specifically and individually incorporated by reference.

The invention now being fully described it will be apparent to one of ordinary skill in the art that many changes and modifications can be made thereto without departing from the spirit or scope of the appended claims.

What is claimed is:

1. An isolated DNA sequence selected from the group consisting of SEQ ID NO:1, SEQ ID NO:6, and SEQ ID NO:9.

2. An isolated DNA sequence which encodes an amino acid sequence selected from the group consisting of SEQ ID NO:2, SEQ ID NO:3, SEQ ID NO:7, and SEQ ID NO:10.

3. A DNA construct comprising:
   at lease one DNA sequence according to claim 1 or 2 operably linked to transcriptional or translational regulatory signals functional in a host cell.

4. A transformed host cell comprising:
   a DNA sequence according to claim 1 or 2.

5. The transformed host cell according to claim 4, wherein said cell is a prokaryote.

6. The transformed host cell according to claim 4, wherein said host cell is selected from the group consisting of an *Escherichia coli*, a Streptoniycete, a *Penicillium chrysogenum*, an *Aspergillus nidulans*, and an *Acremonium chrysogenum*.

7. A method for producing β-lactam compounds, said method comprising growing a transformed host cell according to claim 4, wherein said DNA sequence is operably linked to transcriptional and translational regulatory signals functional in said cell, under conditions whereby said cell produces β-lactam compounds.

8. A method for isolating β-lactam compounds said method comprising:
   growing a host cell transformed with a DNA construct according to claim 3 under conditions whereby β-lactam compounds are produced; and
   isolating said β-lactam compounds.

9. The method according to claim 8, wherein said host cell is a fungus or a prokaryote.

10. The method according to claim 9, wherein said host cell is selected from the group consisting of *Escherichia coli*, Streptomyces, *Penicillium chrysogenum*, *Aspergillus niduilans*, and *Acremonium chrysogenum*.

11. A method for isolating a *Penicillium chrysogenum* oxido reductase system, said method comprising:
   growing a microorganism culture containing cells comprising DNA sequences encoding first and second polypeptide components of said oxido reductase system, wherein said first component comprises a high molecular weight (HMW) polypeptide with a molecular weight of about 36 kDa and said second component comprises a low molecular weight (LMW) polypeptide with a molecular weight of about 12 kDa, wherein each DNA sequence is under the regulatory control of expression signals functional in said cells, whereby said components of said oxido reductase system are expressed; and
   isolating said oxido reductase system.

12. A method for isolating a DNA sequence encoding a polypeptide component of an oxido reductase system comprising first and second components, wherein said first component comprises a high molecular weight (HMW) polypeptide with a molecular weight of about 36 kDa and said second component comprises a low molecular weight (LMW) polypeptide with a molecular weight of about 12 kDa, which said polypeptide component functions in an oxido reductase system to reduce disulfide compounds in the presence of a reduced electron donor, wherein said method comprises;
   (a) obtaining a clone library wherein each clone contains a fragment of DNA from a microorganism, said clone library of a β-lactam producing species;
   (b) screening said clone library for hybridization to an oligonucleotide probe based on the N-terminal amino acid sequence of the *P. chrysogenum* HMW or LMW polypeptide;
   (c) selecting those clones which hybridize to said nucleic acid probe thereby isolating a clone which comprises said DNA sequence, said hybridization being done at 42° C. in a standard hybridization solution containing 15% formamide and involving washing with 1 to 2×SSC at 50° to 60° C.;
   (d) expressing said DNA sequence in a host cell to obtain its encoded polypeptide; and
   (e) assaying whether said polypeptide functions in an oxido reductase system to reduce disulfide compounds in the presence of a reduced electron donor.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 250 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE: Penicillium chrysogenum ( i x ) FEATURE:
( A ) NAME/KEY: exon
( B ) LOCATION: 59..80

( i x ) FEATURE:
( A ) NAME/KEY: intron
( B ) LOCATION: 81..163

( i x ) FEATURE:
( A ) NAME/KEY: exon
( B ) LOCATION: 164..250

( x i ) SEQUENCE DESCRIPTION: SEQ ID NO:1:

```
GCCTCGGTCT  TCTCCAAGTC  ATTTCCGAGC  GTCGCGCGTC  AATTCCAATA  CCGCCAGA                        58

ATG GTG CAC TCT AAA GTA GTC A GTAAGTGGTT TTTCGAGGAG ATCGAATGAT                              110
Met Val His Ser Lys Val Val I
 1               5

CCGGATCACC  TAGATTTCTT  CGATATCAGA  GTTCTAACCG  TTTCCCCCA CA GTT                             165
                                                                 l e
                                                                 1

ATT GGC TCC GGC CCT GGT GCC CAC ACT GCC GCT ATC TAT CTA TCG CGC                             213
Ile Gly Ser Gly Pro Gly Ala His Thr Ala Ala Ile Tyr Leu Ser Arg
         5                       10                      15

GCA GAG CTC CAG CCA GTC CTT TAC GAG GGC ATG CTC G                                           250
Ala Glu Leu Gln Pro Val Leu Tyr Glu Gly Met Leu
         20                      25
```

( 2 ) INFORMATION FOR SEQ ID NO:2:

( i ) SEQUENCE CHARACTERISTICS:
: ( A ) LENGTH: 36 amino acids
: ( B ) TYPE: amino acid
: ( D ) TOPOLOGY: linear ( i i ) MOLECULE TYPE: protein ( v i ) ORIGINAL SOURCE: P. chrysogenum ( i x ) FEATURE:
: ( A ) NAME/KEY: HMW component of the P. chrysogenum oxido reductase system
: ( B ) LOCATION: 1..36

( x i ) SEQUENCE DESCRIPTION: SEQ ID NO:2:

```
Met Val His Ser Lys Val Val Ile Ile Gly Ser Gly Pro Gly Ala His
 1               5                  10                  15
Thr Ala Ala Ile Tyr Leu Ser Arg Ala Glu Leu Gln Pro Val Leu Tyr
                20                  25                  30
Glu Gly Met Leu
            35
```

( 2 ) INFORMATION FOR SEQ ID NO:3:

( i ) SEQUENCE CHARACTERISTICS:
: ( A ) LENGTH: 40 amino acids
: ( B ) TYPE: amino acid
: ( D ) TOPOLOGY: linear ( i i ) MOLECULE TYPE: protein ( i i i ) ORIGINAL SOURCE: P. chrysogenum ( i x ) FEATURE:
: ( A ) NAME/KEY: LMW component of the P. chrysogenum oxido reductase system
: ( B ) LOCATION: 1..40
: ( D ) OTHER INFORMATION: /note="The amino acid at position 34 is unknown."

( x i ) SEQUENCE DESCRIPTION: SEQ ID NO:3:

```
Gly Val Thr Pro Ile Lys Ser Val Ala Glu Tyr Lys Glu Lys Val Thr
 1               5                  10                  15
Asp Ala Thr Gly Pro Val Val Val Asp Phe His Ala Thr Trp Glu Gly
                20                  25                  30
Pro Xaa Lys Ala Ile Ala Pro Glu
            35                  40
```

( 2 ) INFORMATION FOR SEQ ID NO:4:

( i ) SEQUENCE CHARACTERISTICS:
: ( A ) LENGTH: 29 base pairs
: ( B ) TYPE: nucleic acid
: ( C ) STRANDEDNESS: single
: ( D ) TOPOLOGY: linear ( i i ) MOLECULE TYPE: DNA (genomic)

( i v ) ANTI-SENSE: NO ( i x ) FEATURE:
: ( B ) LOCATION: 1..29
: ( D ) OTHER INFORMATION: /note="Nucleotide N at positions 6, 12, 18, 21 and 24 is inosine."

( x i ) SEQUENCE DESCRIPTION: SEQ ID NO:4:

GGHCCNGGHG CNCASACNGC NGCNATYGC    29

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: protein ( i x ) FEATURE:
    ( A ) NAME/KEY: redox sequence typical for thioredoxins
    ( B ) LOCATION: 1..4

( x i ) SEQUENCE DESCRIPTION: SEQ ID NO:5:

```
Cys  Gly  Pro  Cys
1
```

( 2 ) INFORMATION FOR SEQ ID NO:6:

( i ) SEQUENCE CHARACTERISTICS:
        ( A ) LENGTH: 1423 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Penicillium chrysogenum ( i x ) FEATURE:
        ( A ) NAME/KEY: exon
        ( B ) LOCATION: 119..140

( i x ) FEATURE:
        ( A ) NAME/KEY: intron
        ( B ) LOCATION: 141..223

( i x ) FEATURE:
        ( A ) NAME/KEY: exon
        ( B ) LOCATION: 224..1123

( i x ) FEATURE:
        ( A ) NAME/KEY: intron
        ( B ) LOCATION: 1124..1188

( i x ) FEATURE:
        ( A ) NAME/KEY: exon
        ( B ) LOCATION: 1189..1271

( i x ) FEATURE:
        ( A ) NAME/KEY: CDS
        ( B ) LOCATION: join(119..140, 224..1123, 1189..1271)
        ( D ) OTHER INFORMATION: /product="HMW protein"
                / gene= "trxB"

( x i ) SEQUENCE DESCRIPTION: SEQ ID NO:6:

```
GGATCCATTG GGTTGACTGC CACTGCGGCC ACTACCCTTC ACCAACAATC TCCTCCTTCG       60

GCCTCGGTCT TCTCCAAGTC ATTTCCGAGC GTCGCGCGTC AATTCCAATA CCGCCAGA       118

ATG GTG CAC TCT AAA GTA GTC AGTAAGTGGT TTTTCGAGGA GATGGAATGA           169
Met Val His Ser Lys Val Val I
 1               5

TCCGGATCAC CTAGATTTCT TCGATATCAG AGTTCTAACC GTTTTCCCCC ACA GTT         225
                                                                 l e

ATT GGC TCC GGC CCT GGT GCC CAC ACT GCC GCT ATC TAT CTA TCG CGC       273
Ile Gly Ser Gly Pro Gly Ala His Thr Ala Ala Ile Tyr Leu Ser Arg
    10              15                  20

GCA GAG CTC CAG CCA GTC CTT TAC GAG GGC ATG CTC GCC AAC GGT ACC       321
Ala Glu Leu Gln Pro Val Leu Tyr Glu Gly Met Leu Ala Asn Gly Thr
25                  30                  35                  40
```

```
GCC GCC GGT GGT CAG CTC ACG ACG ACC ACT GAC GTC GAG AAC TTC CCC        369
Ala Ala Gly Gly Gln Leu Thr Thr Thr Thr Asp Val Glu Asn Phe Pro
             45                  50                  55

GGA TTC CCC AGC GGC ATC GGC GGC GCC GAG CTC ATG GAC AAC ATG CGC        417
Gly Phe Pro Ser Gly Ile Gly Gly Ala Glu Leu Met Asp Asn Met Arg
             60                  65                  70

GCC CAA TCC GAG CGC TTC GGC ACC GAG ATC ATC ACA GAG ACC ATC TCC        465
Ala Gln Ser Glu Arg Phe Gly Thr Glu Ile Ile Thr Glu Thr Ile Ser
         75                  80                  85

AAG CTT GAC CTC TCC TCC CGG CCC TTC AAG ATG TGG ACC GAG TGG AAC        513
Lys Leu Asp Leu Ser Ser Arg Pro Phe Lys Met Trp Thr Glu Trp Asn
         90                  95                 100

GAT GAC GAA GGC AGC GAG CCC GTC CGC ACC GCC GAC GCC GTC ATC ATT        561
Asp Asp Glu Gly Ser Glu Pro Val Arg Thr Ala Asp Ala Val Ile Ile
105             110                 115                 120

GCC ACA GGC GCC AAC GCC CGC CGT CTG AAC CTG CCC GGC GAG GAG ACC        609
Ala Thr Gly Ala Asn Ala Arg Arg Leu Asn Leu Pro Gly Glu Glu Thr
             125                 130                 135

TAC TGG CAG AAC GGA ATC AGC GCC TGT GCC GTC TGC GAC GGT GCC GTG        657
Tyr Trp Gln Asn Gly Ile Ser Ala Cys Ala Val Cys Asp Gly Ala Val
             140                 145                 150

CCC ATT TTC CGT AAC AAG CCC CTG TAC GTC ATT GGC GGT GGT GAC TCC        705
Pro Ile Phe Arg Asn Lys Pro Leu Tyr Val Ile Gly Gly Gly Asp Ser
             155                 160                 165

GCC GCC GAG GAG GCC ATG TTC CTG GCC AAG TAC GGC AGC AGC GTG ACT        753
Ala Ala Glu Glu Ala Met Phe Leu Ala Lys Tyr Gly Ser Ser Val Thr
             170                 175                 180

GTT CTC GTT CGC AAG GAC AAG CTG CGT GCC TCT AAC ATC ATG GCT GAT        801
Val Leu Val Arg Lys Asp Lys Leu Arg Ala Ser Asn Ile Met Ala Asp
185                 190                 195                 200

CGT CTC CTT GCC CAC CCC AAG TGC AAG GTC CGC TTC AAC ACC GTC GCC        849
Arg Leu Leu Ala His Pro Lys Cys Lys Val Arg Phe Asn Thr Val Ala
             205                 210                 215

ACC GAG GTT ATC GGC GAG AAC AAG CCT AAC GGC CTC ATG ACC CAC CTC        897
Thr Glu Val Ile Gly Glu Asn Lys Pro Asn Gly Leu Met Thr His Leu
             220                 225                 230

CGT GTC AAG GAC GTT CTC TCT AAC GCG GAG GAG GTC GTT GAG GCT AAC        945
Arg Val Lys Asp Val Leu Ser Asn Ala Glu Glu Val Val Glu Ala Asn
             235                 240                 245

GGT CTC TTC TAC GCT GTT GGT CAC GAC CCC GCC AGT GGT CTC GTC AAG        993
Gly Leu Phe Tyr Ala Val Gly His Asp Pro Ala Ser Gly Leu Val Lys
             250                 255                 260

GGC CAG GTT GAG CTC GAC GAC GAG GGA TAC ATC ATC ACC AAG CCC GGT       1041
Gly Gln Val Glu Leu Asp Asp Glu Gly Tyr Ile Ile Thr Lys Pro Gly
265                 270                 275

ACT AGC TTC ACT AAC GTC GAG GGT GTT TTC GCC TGC GGT GAT GTT CAG       1089
Thr Ser Phe Thr Asn Val Glu Gly Val Phe Ala Cys Gly Asp Val Gln
             285                 290                 295

GAT AAG CGC TAC CGT CAG GCT ATC ACC AGT GCC G GTATGTTCAT             1133
Asp Lys Arg Tyr Arg Gln Ala Ile Thr Ser Ala G
             300                 305

ACTTCAGCAT CTCATTCATA GTAATTGCAA TTTGGCTAAC TCAATATTCT ACCA GGA       1190
                                                              ly

TCT GGC TGT GTC GCT GCT CTT GAG GCT GAG AAG TTC ATC GCC GAG ACC       1238
Ser Gly Cys Val Ala Ala Leu Glu Ala Glu Lys Phe Ile Ala Glu Thr
             310                 315                 320

GAG ACT CAC CAG GAG GCA AAG CCT GTG CTC TAAATATATA TACACCCTTT         1288
Glu Thr His Gln Glu Ala Lys Pro Val Leu
325                 330
```

```
CTCCTACTGT  TCTCTCCTAT  TTCTCGTTGT  CATGATGCAT  GAAACATGAT  GTTTGGCGCG   1348

TGTATCGAGG  ATTCTTCTTG  CTTCTAGACT  TATATCTGTT  TTATGCGATG  ACTCTAGAGG   1408

ATCCCCGGGT  ACCGA                                                        1423
```

( 2 ) INFORMATION FOR SEQ ID NO:7:

( i ) SEQUENCE CHARACTERISTICS:
        ( A ) LENGTH: 334 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

```
Met  Val  His  Ser  Lys  Val  Val  Ile  Ile  Gly  Ser  Gly  Pro  Gly  Ala  His
 1              5                         10                       15

Thr  Ala  Ala  Ile  Tyr  Leu  Ser  Arg  Ala  Glu  Leu  Gln  Pro  Val  Leu  Tyr
           20                       25                       30

Glu  Gly  Met  Leu  Ala  Asn  Gly  Thr  Ala  Ala  Gly  Gly  Gln  Leu  Thr  Thr
      35                       40                       45

Thr  Thr  Asp  Val  Glu  Asn  Phe  Pro  Gly  Phe  Pro  Ser  Gly  Ile  Gly  Gly
 50                            55                       60

Ala  Glu  Leu  Met  Asp  Asn  Met  Arg  Ala  Gln  Ser  Glu  Arg  Phe  Gly  Thr
65                       70                       75                       80

Glu  Ile  Ile  Thr  Glu  Thr  Ile  Ser  Lys  Leu  Asp  Leu  Ser  Ser  Arg  Pro
                     85                       90                       95

Phe  Lys  Met  Trp  Thr  Glu  Trp  Asn  Asp  Glu  Gly  Ser  Glu  Pro  Val
               100                      105                      110

Arg  Thr  Ala  Asp  Ala  Val  Ile  Ile  Ala  Thr  Gly  Ala  Asn  Ala  Arg  Arg
           115                      120                      125

Leu  Asn  Leu  Pro  Gly  Glu  Glu  Thr  Tyr  Trp  Gln  Asn  Gly  Ile  Ser  Ala
130                      135                      140

Cys  Ala  Val  Cys  Asp  Gly  Ala  Val  Pro  Ile  Phe  Arg  Asn  Lys  Pro  Leu
145                      150                      155                      160

Tyr  Val  Ile  Gly  Gly  Gly  Asp  Ser  Ala  Ala  Glu  Glu  Ala  Met  Phe  Leu
                     165                      170                      175

Ala  Lys  Tyr  Gly  Ser  Ser  Val  Thr  Val  Leu  Val  Arg  Lys  Asp  Lys  Leu
           180                      185                      190

Arg  Ala  Ser  Asn  Ile  Met  Ala  Asp  Arg  Leu  Leu  Ala  His  Pro  Lys  Cys
           195                      200                      205

Lys  Val  Arg  Phe  Asn  Thr  Val  Ala  Thr  Glu  Val  Ile  Gly  Glu  Asn  Lys
     210                      215                      220

Pro  Asn  Gly  Leu  Met  Thr  His  Leu  Arg  Val  Lys  Asp  Val  Leu  Ser  Asn
225                      230                      235                      240

Ala  Glu  Glu  Val  Val  Glu  Ala  Asn  Gly  Leu  Phe  Tyr  Ala  Val  Gly  His
                     245                      250                      255

Asp  Pro  Ala  Ser  Gly  Leu  Val  Lys  Gly  Gln  Val  Glu  Leu  Asp  Asp  Glu
           260                      265                      270

Gly  Tyr  Ile  Ile  Thr  Lys  Pro  Gly  Thr  Ser  Phe  Thr  Asn  Val  Glu  Gly
           275                      280                      285

Val  Phe  Ala  Cys  Gly  Asp  Val  Gln  Asp  Lys  Arg  Tyr  Arg  Gln  Ala  Ile
     290                      295                      300

Thr  Ser  Ala  Gly  Ser  Gly  Cys  Val  Ala  Ala  Leu  Glu  Ala  Glu  Lys  Phe
305                      310                      315                      320

Ile  Ala  Glu  Thr  Glu  Thr  His  Gln  Glu  Ala  Lys  Pro  Val  Leu
                325                      330
```

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Penicillium chrysogenum
        ( C ) INDIVIDUAL ISOLATE: ex9

( i x ) FEATURE:
        ( A ) NAME/KEY: misc feature
        ( B ) LOCATION: 1..29
        ( D ) OTHER INFORMATION: /note= "Nucleotide N at positions 3, 6, 24, 27 are inosine."

( x i ) SEQUENCE DESCRIPTION: SEQ ID NO:8:

```
TCNGTNACYT TYTCYTTRTA YTCNGCNAC                                29
```

( 2 ) INFORMATION FOR SEQ ID NO:9:

( i ) SEQUENCE CHARACTERISTICS:
        ( A ) LENGTH: 914 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Penicillium chrysogenum ( i x ) FEATURE:
        ( A ) NAME/KEY: exon
        ( B ) LOCATION: 384..406

( i x ) FEATURE:
        ( A ) NAME/KEY: intron
        ( B ) LOCATION: 407..545

( i x ) FEATURE:
        ( A ) NAME/KEY: exon
        ( B ) LOCATION: 546..843

( i x ) FEATURE:
        ( A ) NAME/KEY: CDS
        ( B ) LOCATION: join(384..406, 546..843)
        ( D ) OTHER INFORMATION: /product="LMW protein"
        / gene= "trxA"

( x i ) SEQUENCE DESCRIPTION: SEQ ID NO:9:

```
GTACTAGTAC  TGACAAATCT  CACCATGTAA  GTCCCAATTG  AAATCTTCCC  CTTGGAAGAA      60
TCCCGATCAA  ACCAGCAAAG  CTCCAGAGAC  TTCTGGACCT  TCAGACGGGG  CCAGCTCGAC     120
CCATTATTCA  GCGCGTCTTA  CCTAATCCCC  TCTGCTGGCC  CCGGCGAACG  TCATGGCCCT     180
ATAAAAACCT  AACGCCCCTC  ACTCTACCCC  TCCAATCGAA  ATACTCATAT  CCACTCCAGT     240
TCAAGCCTTC  AACTCTTCGT  TCTACCCCCA  GAACCATCTC  CGGAGTTTCA  TCGCTACTCA     300
ATCGATCGAC  TTCCGTCCAG  CGCGCCGCTT  TCCGACCCTT  TTCTTCCACA  CCTATCCCCC     360
```

```
GCTTCACGCC TTCATCTCTC AAA ATG CGT GTC ACT CCT ATC AAG TCG T            408
                         Met Arg Val Thr Pro Ile Lys Se
                          1                 5

AAGTCCGACC TTACTCTCAT ATTCCCGCTT TCGGTTCTGT ATCTGGATCC CAGAAACATG       468

CCCTACACAC TCGTGATCAT TTCGCAAGAC ATCGTTTGT ACAACATCAC AGACAACCCA        528

GCTAATACTC CTCACAGC GTC GCC GAG TAC AAG GAA AAG GTC ACC GAC             576
                  r Val Ala Glu Tyr Lys Glu Lys Val Thr Asp
                    10                  15

GCC ACC GGC CCC GTC GTC GTC GAC TTC CAC GCC ACC TGG TGC GGT CCC         624
Ala Thr Gly Pro Val Val Val Asp Phe His Ala Thr Trp Cys Gly Pro
20              25                          30

TGC AAG GCC ATC GCC CCT GCC CTC GAG AAG CTC AGC GAG ACC CAC ACC         672
Cys Lys Ala Ile Ala Pro Ala Leu Glu Lys Leu Ser Glu Thr His Thr
35              40              45                          50

GGC ATC CAG TTC TAC AAG GTC GAC GTC GAT GAG CTC TCT GAG GTC GCT         720
Gly Ile Gln Phe Tyr Lys Val Asp Val Asp Glu Leu Ser Glu Val Ala
                55              60                          65

GCT TCC AAC GGC GTC TCT GCT ATG CCT ACC TTC CAC TTC TAC AAG GGT         768
Ala Ser Asn Gly Val Ser Ala Met Pro Thr Phe His Phe Tyr Lys Gly
            70              75                          80

GGT GAG CGC AAC GAG GAG GTT AAG GGT GCT AAC CCT GCT GCC ATC CAG         816
Gly Glu Arg Asn Glu Glu Val Lys Gly Ala Asn Pro Ala Ala Ile Gln
        85                  90                      95

GCT GGC GTC AAG GCT ATC CTT GAA TAGATTTGGA ATTGAGATT CGTGCTTGAT         870
Ala Gly Val Lys Ala Ile Leu Glu
    100                 105

CATACCATTC ATCTATGTTT TTTTTCTGA GGGATGGGCA ATCT                         914
```

( 2 ) INFORMATION FOR SEQ ID NO:10:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Arg Val Thr Pro Ile Lys Ser Val Ala Glu Tyr Lys Glu Lys Val
 1               5                  10                      15

Thr Asp Ala Thr Gly Pro Val Val Val Asp Phe His Ala Thr Trp Cys
            20                  25                      30

Gly Pro Cys Lys Ala Ile Ala Pro Ala Leu Glu Lys Leu Ser Glu Thr
                35                  40                  45

His Thr Gly Ile Gln Phe Tyr Lys Val Asp Val Asp Glu Leu Ser Glu
        50                  55                  60

Val Ala Ala Ser Asn Gly Val Ser Ala Met Pro Thr Phe His Phe Tyr
65                  70                  75                  80

Lys Gly Gly Glu Arg Asn Glu Glu Val Lys Gly Ala Asn Pro Ala Ala
                    85                  90                  95

Ile Gln Ala Gly Val Lys Ala Ile Leu Glu
                100                 105
```

( 2 ) INFORMATION FOR SEQ ID NO:11:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( v i ) ORIGINAL SOURCE: P. chrysogenum ( i x ) FEATURE:
    ( A ) NAME/KEY: HMW component of the P. chrysogenum gene.
    ( B ) LOCATION: 1..28
    ( C ) OTHER INFORMATION: /label=alternatives
        / note= "aa1=probably Val, aa2=probably His, aa23=probably Arg."

( x i ) SEQUENCE DESCRIPTION: SEQ ID NO:11:

```
Val His Ser Lys Val Val Ile Ile Gly Ser Gly Pro Gly Ala His Thr
 1               5                  10                  15
Ala Ala Ile Tyr Leu Ser Arg Ala Glu Leu Gln Pro
                20                  25
```